US009632800B1

(12) United States Patent
Chorley et al.

(10) Patent No.: US 9,632,800 B1
(45) Date of Patent: Apr. 25, 2017

(54) TOOLTIP SYSTEM AND METHOD

(71) Applicant: ALLSCRIPTS SOFTWARE, LLC, Chicago, IL (US)

(72) Inventors: Mary Drechsler Chorley, Raleigh, NC (US); Leo Benson, Raleigh, NC (US); Melpakkam Sundar, Morrisville, NC (US); John Lusk, Chapel Hill, NC (US); Cassio Nishiguchi, Raleigh, NC (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 102 days.

(21) Appl. No.: 14/170,560

(22) Filed: Jan. 31, 2014

(51) Int. Cl.
*G06F 3/0481* (2013.01)
*G06F 9/44* (2006.01)
*G06F 3/0485* (2013.01)
*G06F 17/30* (2006.01)

(52) U.S. Cl.
CPC .......... *G06F 9/4446* (2013.01); *G06F 3/0485* (2013.01); *G06F 3/04817* (2013.01); *G06F 17/30* (2013.01); *G06F 17/30882* (2013.01)

(58) Field of Classification Search
CPC .............. G06F 3/0481; G06F 3/04812; G06F 17/30882
USPC ................................ 715/711, 715, 808, 809
See application file for complete search history.

(56) References Cited

U.S. PATENT DOCUMENTS

| | | | | |
|---|---|---|---|---|
| 6,714,201 | B1* | 3/2004 | Grinstein et al. | 345/474 |
| 2003/0179223 | A1* | 9/2003 | Ying | G06F 3/0482 715/702 |
| 2004/0017404 | A1* | 1/2004 | Schileru-Key | 345/854 |
| 2006/0161855 | A1* | 7/2006 | Robertson et al. | 715/765 |
| 2008/0133553 | A1* | 6/2008 | Kitsis et al. | 707/100 |
| 2010/0070872 | A1* | 3/2010 | Trujillo | 715/745 |
| 2011/0208718 | A1* | 8/2011 | Tarjan | 707/711 |
| 2014/0372943 | A1* | 12/2014 | Kroupa et al. | 715/808 |

OTHER PUBLICATIONS

Screenshots of Microsoft Outlook (release date Jan. 29, 2013, pp. 1-3).*

* cited by examiner

*Primary Examiner* — Doon Chow
*Assistant Examiner* — Le Nguyen
(74) *Attorney, Agent, or Firm* — Tillman Wright, PLLC; Chad D. Tillman; Jeremy C. Doerre

(57) ABSTRACT

A method for accessing information in a software application using a computing device, the computing device comprising one or more processors, the one or more processors for executing a plurality of computer readable instructions, the computer readable instructions for implementing the method for accessing information, the method comprising the steps of determining that a pointer is hovering over an icon, the icon associated with icon specific information, displaying a Tooltip including a heading, a display window and an action button, the action button for launching an action in the application, displaying the icon specific information in the display window, detecting that a user has selected the action button, and launching the action.

15 Claims, 8 Drawing Sheets

TOOLTIP SYSTEM AND METHOD

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention relates to a computing device. More specifically, the present invention relates to navigating within a software application.

In software applications, information is available to users in many areas in a user interface (UI). As the amount of information that is available for display increases, some information may be hidden in the UI and accessible on another page, another window, etc. Quick and easy access to information wherever it is located has become ever so important.

One method used in applications to view relevant information is through a pop-up window. Current pop-up windows only display the information. If other relevant information is available in the application that may be related to the information in the window, the user is has to access the other information by clicking on an item outside the open pop-up window.

As an example, in a healthcare software application that includes a Status Board in an Emergency Department, if a user wanted to order status information, access a new order, and new result information, the user would have to double-click separate icons to see that information. In such an environment, the ability to quickly view patient information with minimal navigation would be beneficial to healthcare providers.

Therefore, there exists a need for an improved method for accessing relevant information in a software application. This and other needs are addressed by one or more aspects of the present invention.

SUMMARY OF THE INVENTION

The present invention includes many aspects and features. Moreover, while many aspects and features relate to, and are described in, the context of healthcare applications, the present invention is not limited to use only in this context, as will become apparent from the following summaries and detailed descriptions of aspects, features, and one or more embodiments of the present invention.

Accordingly, one aspect of the present invention relates to a method for accessing information in a software application using a computing device. The computing device comprising one or more processors, the one or more processors for executing a plurality of computer readable instructions. The computer readable instructions for implementing the method for accessing information, the method comprising the steps of determining that a pointer is hovering over an icon, the icon associated with icon specific information, displaying a Tooltip including a heading, a display window and an action button, the action button for launching an action in the application, displaying the icon specific information in the display window, detecting that a user has selected the action button, and launching the action.

In a feature of this aspect, wherein the method further comprises deleting the Tooltip when the action is launched.

In another feature of this aspect, the Tooltip further includes a tree section including a section of information for review by the user, and a hyperlink for scrolling the section to the top of the display window.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
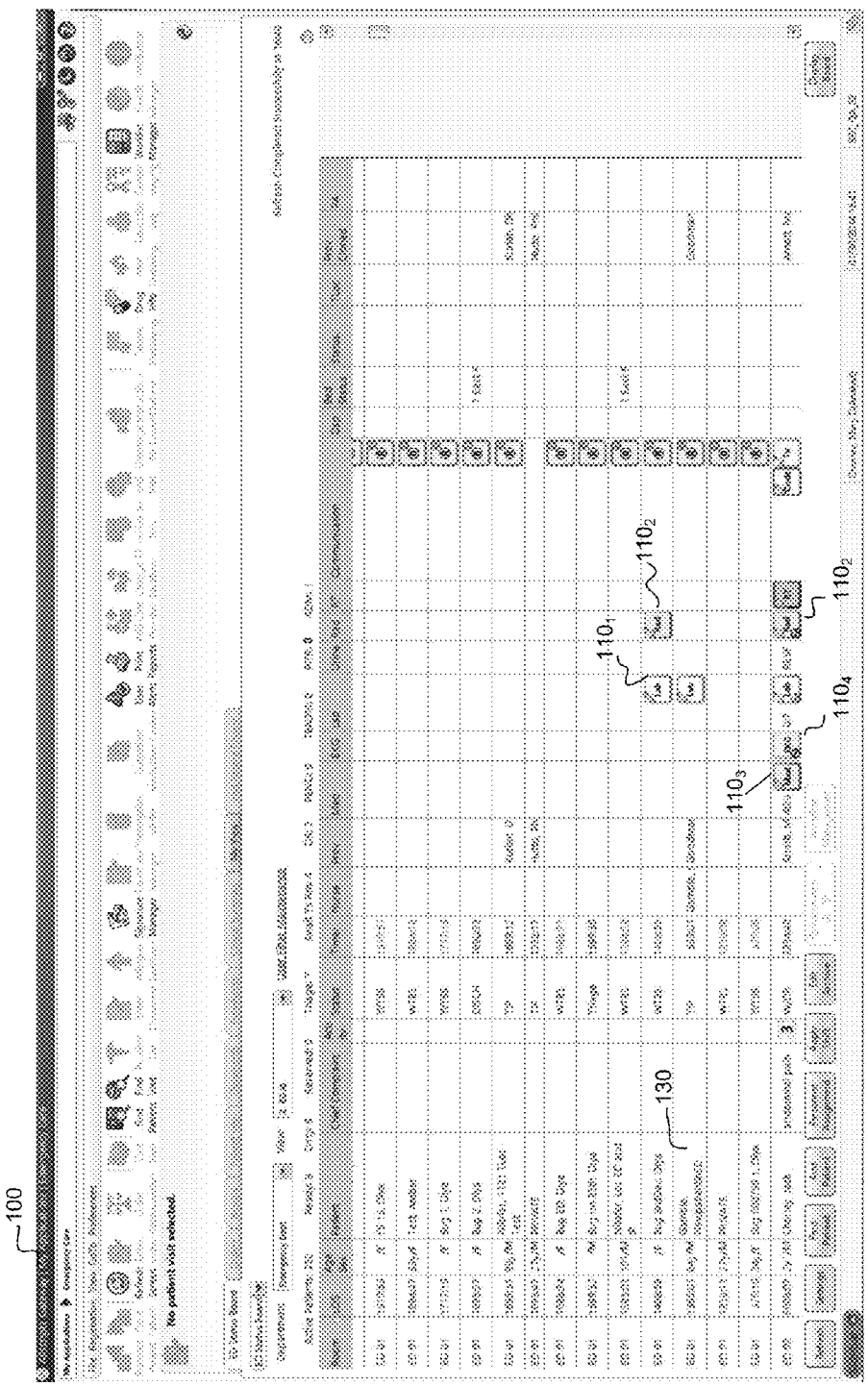
FIG. 1 is an example illustration of an electronic Status Board included in a healthcare application that may be used in an emergency department of a healthcare facility.

Referring now to the drawings, one or more preferred embodiments of the present invention are next described. The following description of one or more preferred embodiments is merely exemplary in nature and is in no way intended to limit the invention, its implementations, or uses.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

A computing device may be any type of device configured to operate and/or communicate in a wired and/or wireless environment. By way of example, the computing device may be configured to transmit and/or receive wireless signals. The computing device includes a memory for storing, for example, an interactive application, and a processor.

The interactive application (software) comprises a set of machine readable code stored on a machine readable medium and is executed by a processor included in the computing device. The application provides user interface tools in the form of graphical screen displays which allow the user to access information.

An implementation of the disclosed Tooltip allows a user to hover over an icon (i.e., an item in the user interface of an application) to view the defined content that applies to the icon. The Tooltip is a pop-up window that includes navigation within the window and action buttons to launch actions in the application in one step, eliminating navigation steps that are usually required by the user to launch the same action somewhere else in the application. For purposes of this disclosure, a healthcare software application will be used as an example. As those skilled in the art should recognize, the disclosed Tooltip may be used in any software application.

FIG. 1 is an example illustration of an electronic Status Board included in a healthcare application that may be used in an emergency department of a healthcare facility. As shown, the Status Board 100 includes a plurality of information icons $110_1 \ldots 110_n$, wherein each icon is associated with patient specific information relevant to the specific icon. For example, patient NewpatientInED 130 on the Status Board has a LAB icon $110_1$ included on the NewpatientInED's 130 row on the board. Other icons displayed in the example include RAD icon $110_2$, MED icon $110_3$, EKG icon $110_4$, etc.

Figure 2:
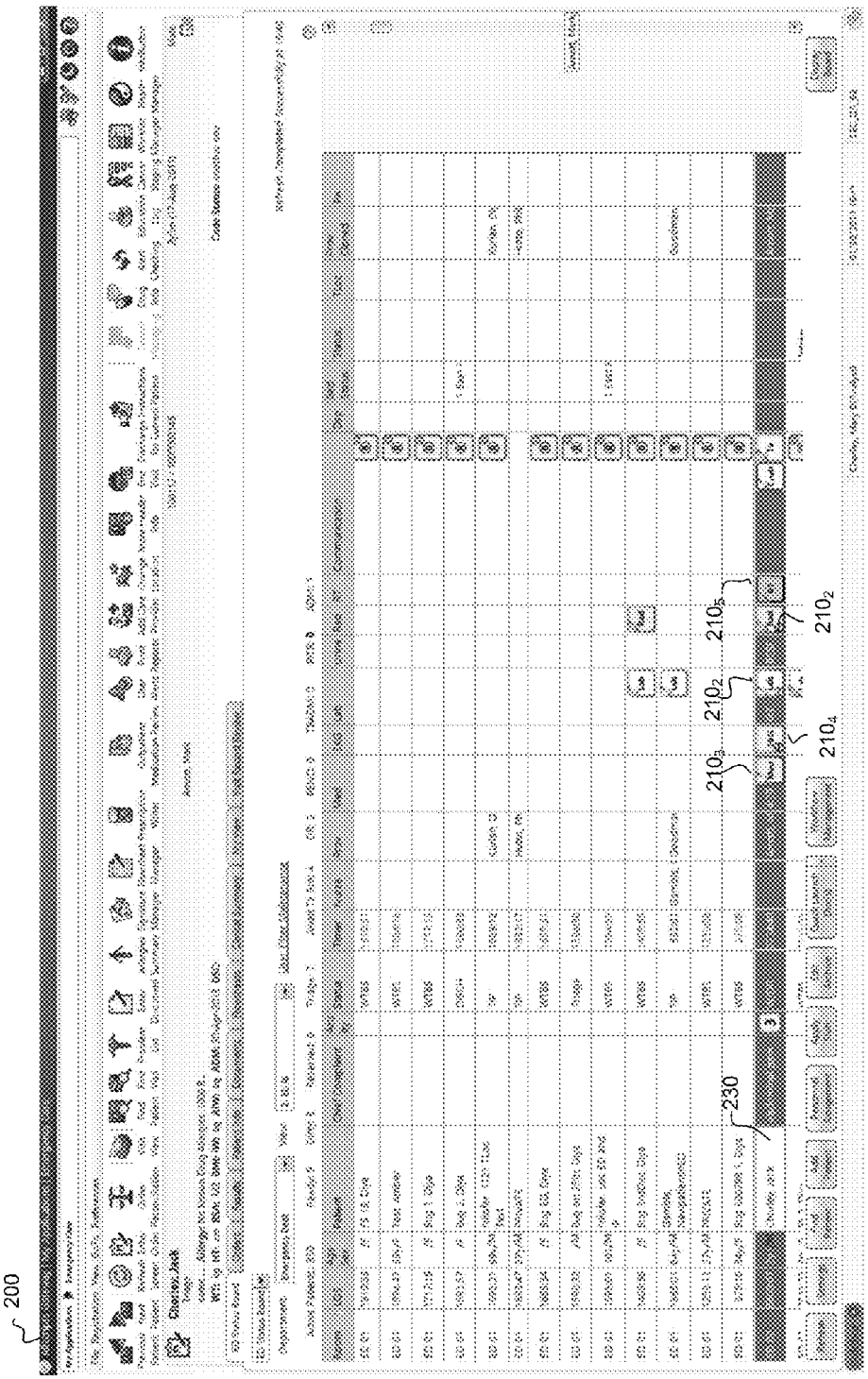
FIG. 2 is an example illustration of the Status Board 100 shown in FIG. 1 after a user has selected a specific patient.

FIG. 2 is an example illustration of the Status Board 100 shown in FIG. 1 after a user has selected a specific patient. As shown in FIG. 2, the selected patient is highlighted and the context is changed to the selected patient. The selected patient in this example, Jack 230, has a plurality of icons in the row, for example, MED icon $210_3$, EKG icon $210_4$, etc.

In accordance with an implementation of the disclosed Tooltip, a user may hover over one of the icons in a patient row and review the information related to the icon in the context of the patient when the Tooltip is displayed. The patient may be the same patient that is highlighted on the Status Board or a different patient. The context of the Tooltip is based on what patient row the icon is located. If a displayed Tooltip is for a patient that is not highlighted, the context of the Status Board does not change. The context of the displayed Tooltip though reflects the patient associated with the icon being hovered over (to be disclosed further hereinafter).

In order to prevent the "visual noise" of many Tooltips popping up as the user is moving his/her pointer (mouse) over the Status Board, it is preferable that the Tooltip only be displayed when the pointer is not moving and is positioned over an icon for a predefined period of time. Accordingly, if the mouse is positioned over an icon for less than the predefined period of time, the Tooltip will not be displayed.

It is also preferable that when the user hovers over an icon and does not move their pointer after the Tooltip is displayed, the Tooltip will be automatically closed after a predefined period of time. Automatically closing the Tooltip prevents sensitive patient data from being displayed in the Tooltip when the user is logged in, hovers over an icon, intentionally or not, and steps away.

The Tooltip is also automatically closed when the user moves the pointer outside of the Tooltip.

Figure 3:
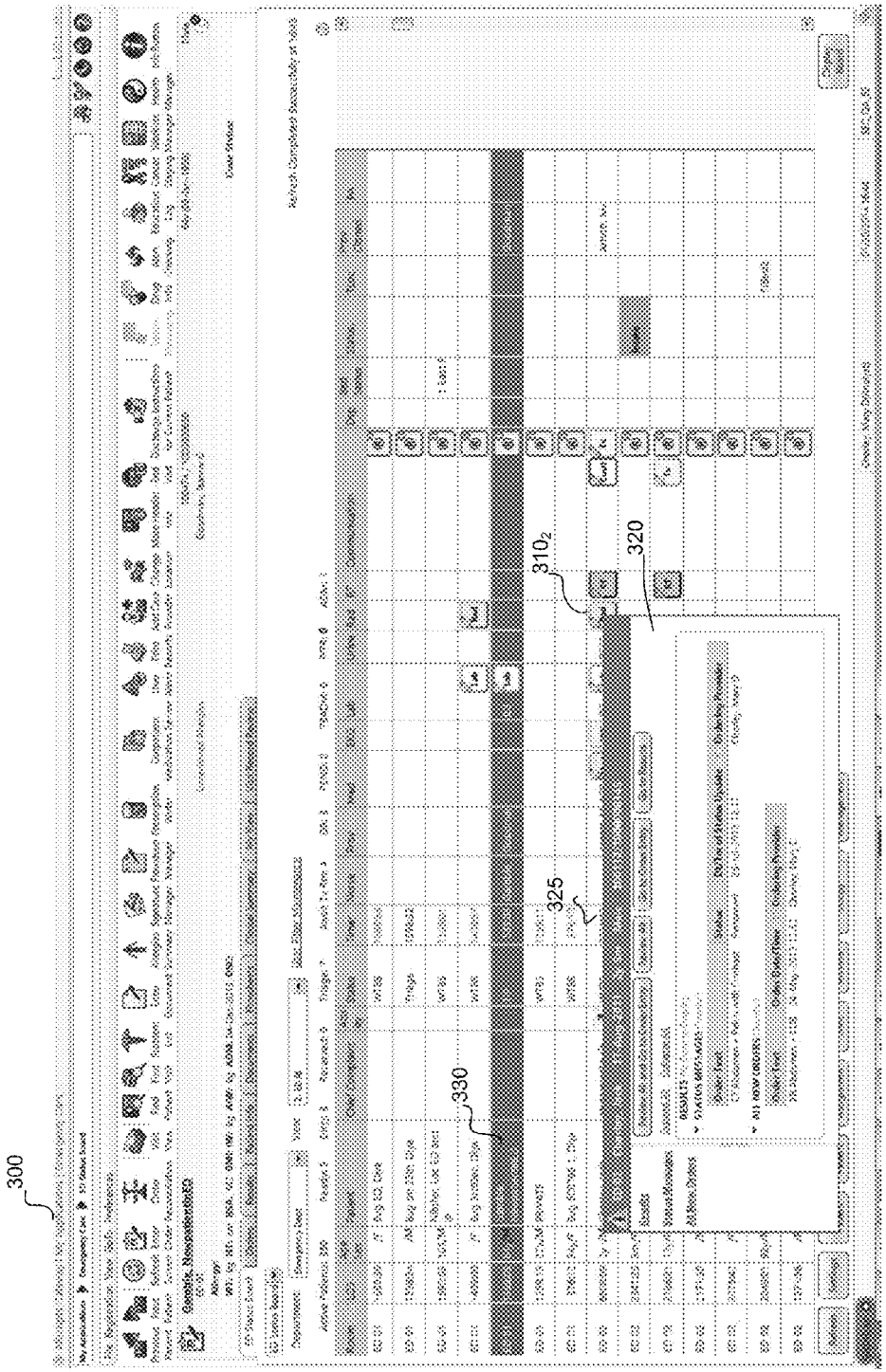
FIG. 3 is an example illustration of an implementation of the disclosed Tooltip displayed on the Status Board in accordance with the present invention.

When the Tooltip is displayed, it is preferable that the Tooltip consistently display in the same location relative to the icon to eliminate the possibility of the Tooltip covering the pointer or the user not knowing which icon the user is hovering over. In accordance with the disclosed Tooltip, the Tooltip is displayed such that the corner of the Tooltip window is located on a portion of the hovered over icon. An example of the Tooltip displayed on the Status Board is illustrated in FIG. 3. As illustrated in FIG. 3, Tooltip 320 is displayed on the Status Board 300 within the grid location of the icon, Rad icon $310_2$. In this display location, the user is able to view the icon for which the user's pointer is hovering over. Although not shown, the user's pointer is displayed within the Tooltip so that the user may navigate within the Tooltip.

As disclosed above, the Tooltip is displayed when the user hovers over an icon on the Status Board, regardless of whether the icon is associated with a selected patient. Referring again to FIG. 3, the selected patient NewpatientInED 330 is highlighted on the Status Board. As illustrated, the Tooltip 320 being displayed is associated with the relevant information for the RAD icon $310_2$ associated with the patient Jack. Since the patient does not have to actually be selected by the user to view the Tooltip, it is preferable that a limited amount of demographic information related to the patient associated with the hovered over icon be displayed in the Tooltip header 325. A context indication may also be displayed in the header 325 that provides a visual indication to the user that the patient associated with the displayed Tooltip is different than the highlighted patient 330. The context indication may include a caution symbol in the header, for example, or the header in the Tooltip may be a certain color that alerts the user, such as the color red. Another example Tooltip of a patient not highlighted on the Status Board is illustrated in FIG. 4.

Figure 4:
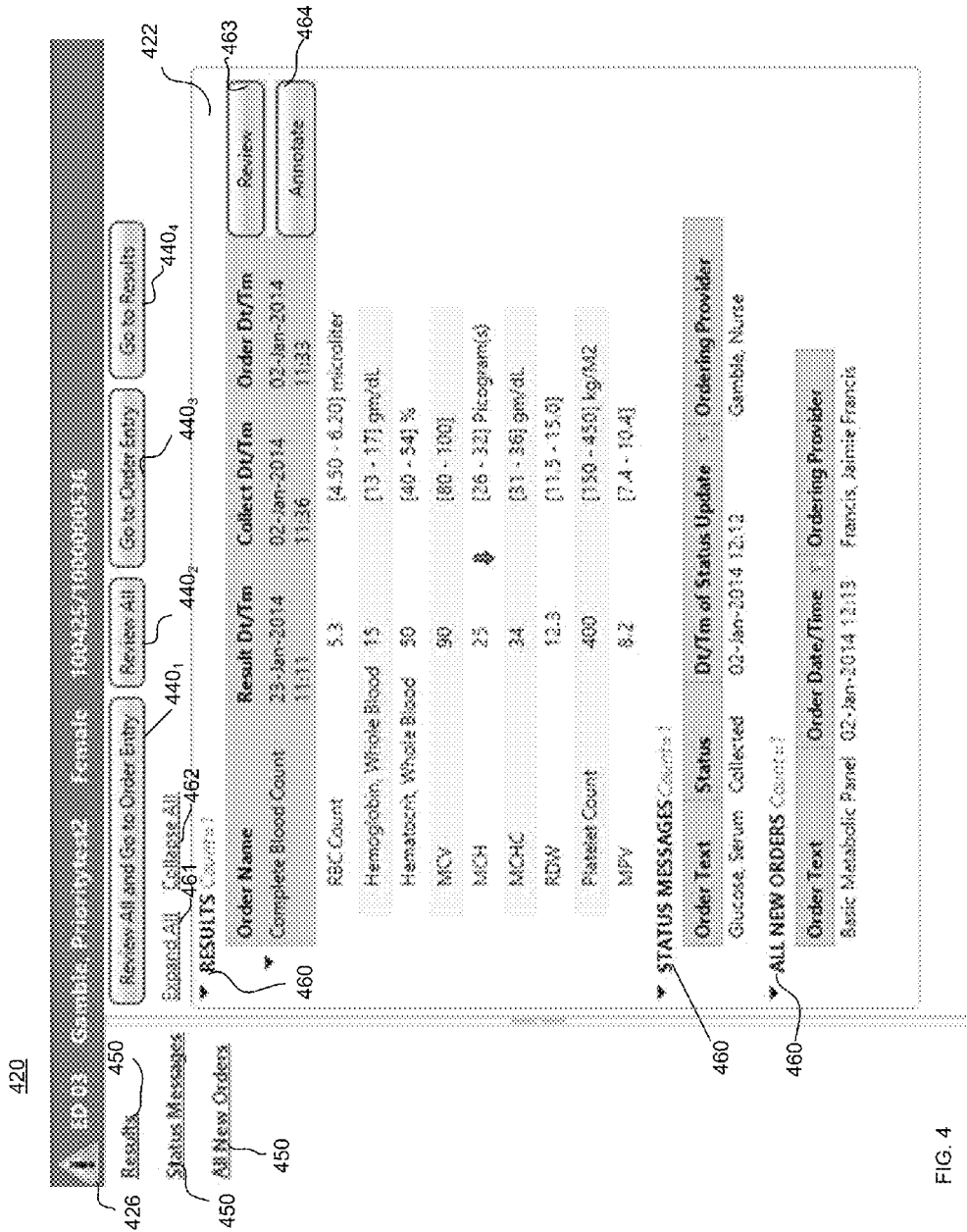
FIG. 4 is an example illustration of the disclosed Tooltip of a patient not highlighted on the Status Board in accordance with present the invention.

Referring to FIG. 4, the Tooltip 420, includes the header 425 and a context indication 426, e.g., caution symbol. The header 425 is also displayed with a dark color (e.g., red) as another context indication.

As set forth above, the disclosed Tooltip 420 includes information related to the associated icon. The Tooltip 420 also includes hyperlinks 450, buttons 440, and tree sections 460. In the example Tooltip 420, the hyperlinks 450 are located on the left of the Tooltip 420, and allow the user to quickly scroll to the associated tree section 460 of the Tooltip. When the user selects the hyperlink 450, the tree section 460 associated with the selected hyperlink 450 is oriented at the top of the Tooltip window 422.

The Tooltip buttons 440 are displayed to the right of the hyperlinks 450 across the top of the window 422. The buttons $440_n$ perform certain defined actions that preferably mirror functions available elsewhere within the healthcare application. In the example shown, the buttons 440 perform the following functions respectively, Review All and Go to Order Entry $440_1$, Review All $440_2$, Go to Order Entry $440_3$, and Go to Results $440_4$.

The tree sections 460 are displayed within the window 422 of the Tooltip 420. As indicated, the user may quickly scroll to a certain tree section 460 by selecting the associated hyperlink 450, or by moving the user's pointer to desired tree section 460. It is preferable that when the Tooltip is opened, the tree sections 460 are displayed in expanded. The user though may collapse or expand the tree sections 460 by selecting tree hyperlinks 462, 461, respectively.

Within the tree sections 460, the capability for the user to perform an action is provided using tree section buttons 463, 464. In the illustrated example, the Results tree section 460 requires a user to acknowledge that the user has reviewed the results, and/or input an annotation associated with the result. This capability is provided by tree section buttons 463, 464 respectively.

When the user selects the Annotate button 464, a fly-out window (not shown) will appear, preferably anchored to the corner of the Annotate button 464. This fly-out window is where the user is able to type in a note, for example. Once the user has completed the annotation, the annotation is saved.

When the Review button 463 is selected, the individual result is acknowledged. It is preferable that the result, once acknowledged, be removed from the Tooltip 420.

In example Tooltip 420, when the Review All button $440_2$ is selected, all results in the Results tree function 460 are marked as reviewed and removed from the Tooltip. Those results that are unable to be acknowledged using the Review All button $440_2$, the result remains in the window and a message is displayed to the user indicating the reason the result cannot be acknowledged in this manner, e.g., critical results must be acknowledged individually.

When the Go to Results button $440_4$ is selected, the Tooltip 420 closes and the user is navigated to Results Tab on the Status Board. If the Tooltip 420 is being displayed for a patient that is not highlighted (i.e., not in context), the patient context is changed on the Status Board. Prior to changing the context, a "Changing Patient Context" message is preferably displayed in a dialog that doesn't require user action. If the context cannot be changed, the Tooltip 420 is closed and a warning message displayed to the user.

Selection of the Go to Order Entry button $440_2$ results in the Tooltip 420 being closed and an Order Entry Worksheet opened. Similar to the Go to Results button $440_4$, if the Tooltip 420 is being displayed for a patient that is not highlighted (i.e., not in context), the patient context is changed on the Status Board. Prior to changing the context, a "Changing Patient Context" message (not shown) is preferably displayed in a dialog that doesn't require user action. If the context cannot be changed, the Tooltip 420 is closed and a warning message displayed to the user. An example illustration of the selection of the Go to Order Entry button by a user is shown in FIG. 5.

Figure 5:
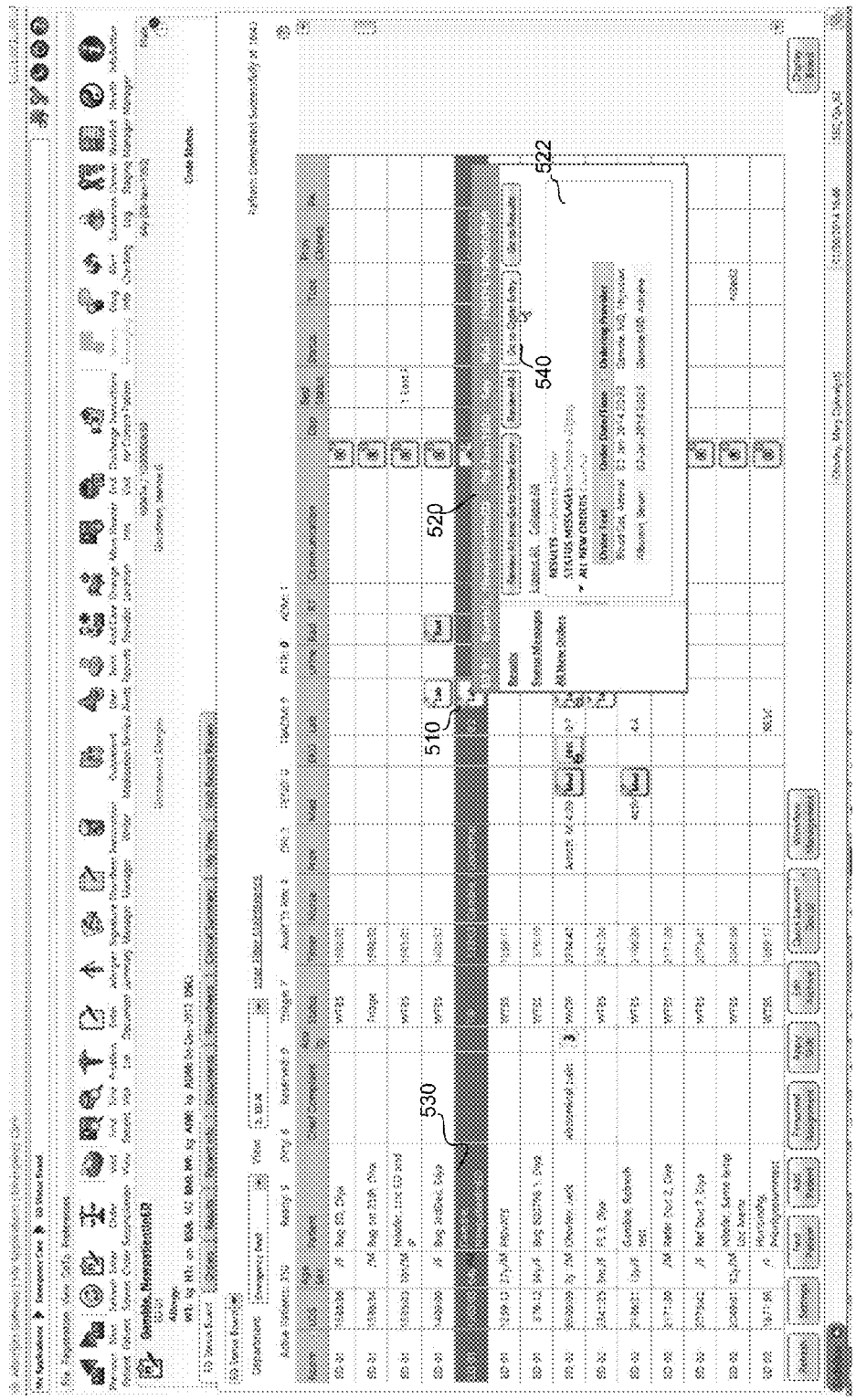
FIG. 5 is an example illustration of the selection of the Go to Order Entry button by a user in the disclosed Tooltip in accordance with the present invention.

Referring to FIG. 5, in the example illustrated, a user has selected a patient 530, NewpatientInED, and hovered the pointer over the LAB icon 510. The Tooltip 520 is displayed and the user has moved the pointer over the Go to Order Entry button 540 in the Tooltip 520 window 522. When the user selects the Go to Order Entry button 540, the Order Entry worksheet is displayed. An example illustration of the Order Entry Worksheet as displayed when selected by the user in the Tooltip 520 is shown in FIG. 6.

Figure 6:
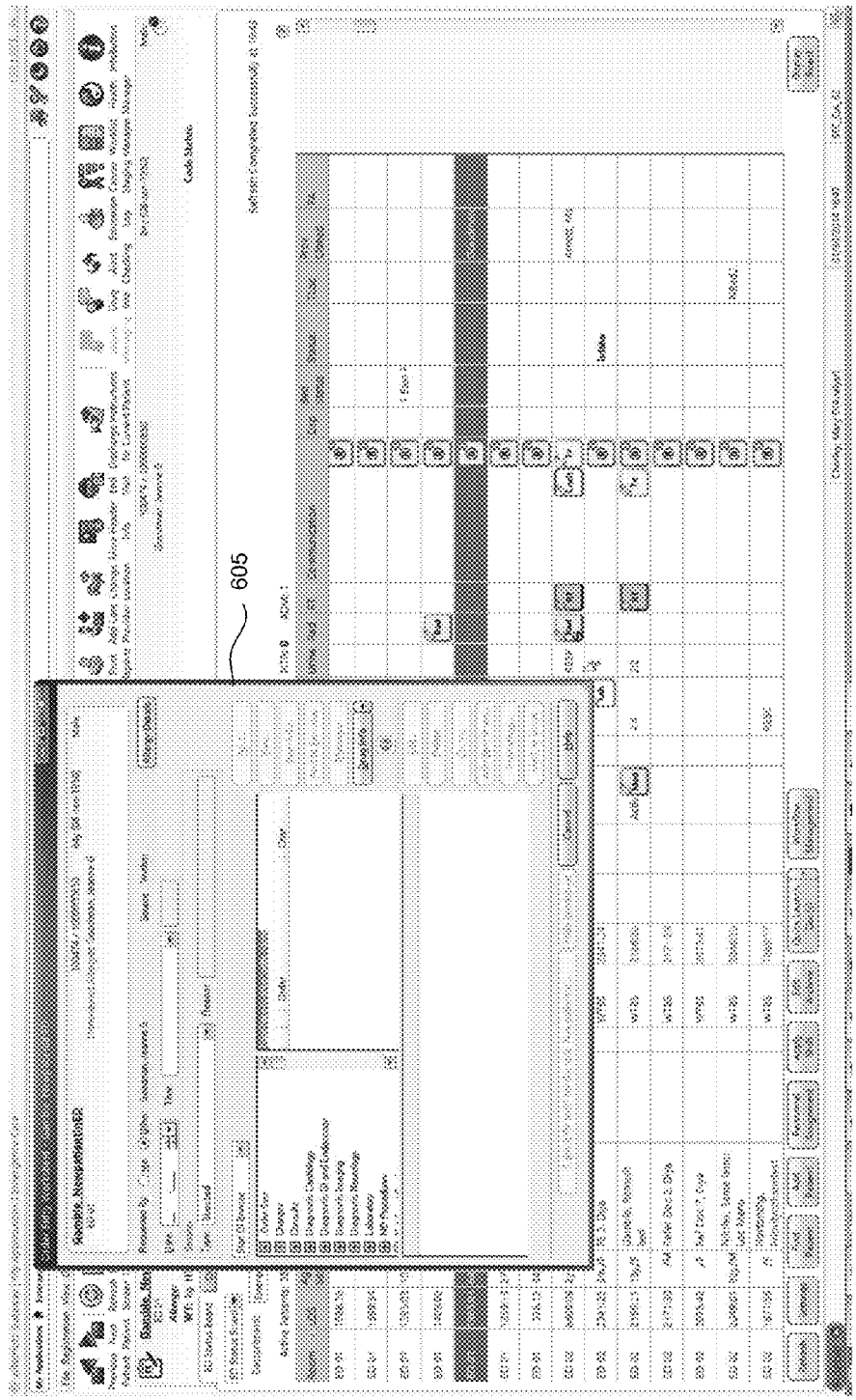
FIG. 6 is an example illustration of the Order Entry Worksheet as displayed when selected by the user in the Tooltip in accordance with the present invention.

Referring to FIG. 6, the Order Entry Worksheet 605 is displayed in the user interface as it would be displayed if the user had navigated to Order Entry other than through the Tooltip.

Referring back to FIG. 4, when the user selects the Review All and Go to Order Entry button $440_1$, all of the results in the Tooltip will be marked as acknowledged, removed from the Tooltip 420 and the Tooltip 420 closed. The Order Entry Worksheet will then open, as exemplified in FIG. 6.

If there are results that cannot be acknowledged and require them to be acknowledged individually, those results will stay in the Tooltip and a message will be displayed explaining why some of the results could not be acknowledged. Once the message is addressed, the Tooltip is closed and the Order Entry Worksheet is opened.

If the Tooltip 420 is being displayed for a patient who is not in context, the patient context is changed as disclosed above for buttons $440_3$ and $440_4$.

Figure 7:
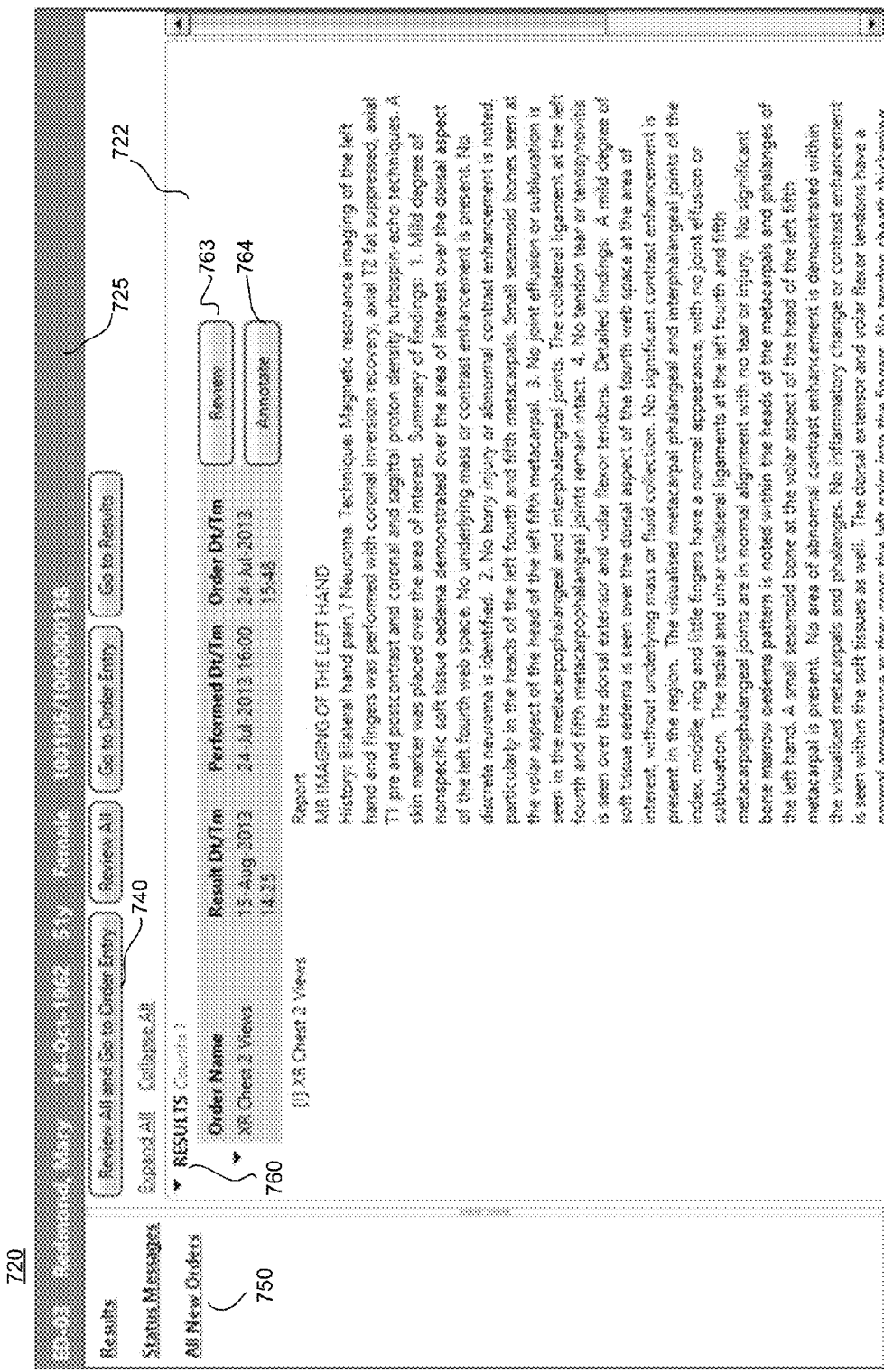
FIG. 7 is an example illustration of a Tooltip that is displayed when a user hovers over an icon in the example Status Board of FIG. 1.

Another example illustration of a Tooltip that is displayed when a user hovers over an icon on the example Status Board of FIG. 1 is shown in FIG. 7. In FIG. 7, the Tooltip 720 displayed is the result of the user hovering on a RAD icon $110_2$, illustrated in FIG. 1. The Tooltip 720 is displayed for a patient that is in context, i.e., highlighted on the Status Board. As illustrated in FIG. 4, the Tooltip 720 includes a header 725, hyperlinks 750, buttons 740, and tree functions 760. The tree section 760 is displayed in the window 722. Tree section buttons 763 and 764 are also included for those parts of the tree section that require an acknowledgement by the user, or allow the user to add an annotation.

In accordance with the disclosed Tooltip, actions taken within the Tooltip, for example acknowledgement of results, are reflected throughout the application and reflected where appropriate on the Status Board. For example, the Status Board icons will be updated based on the rules set for the respective column.

Figure 8:
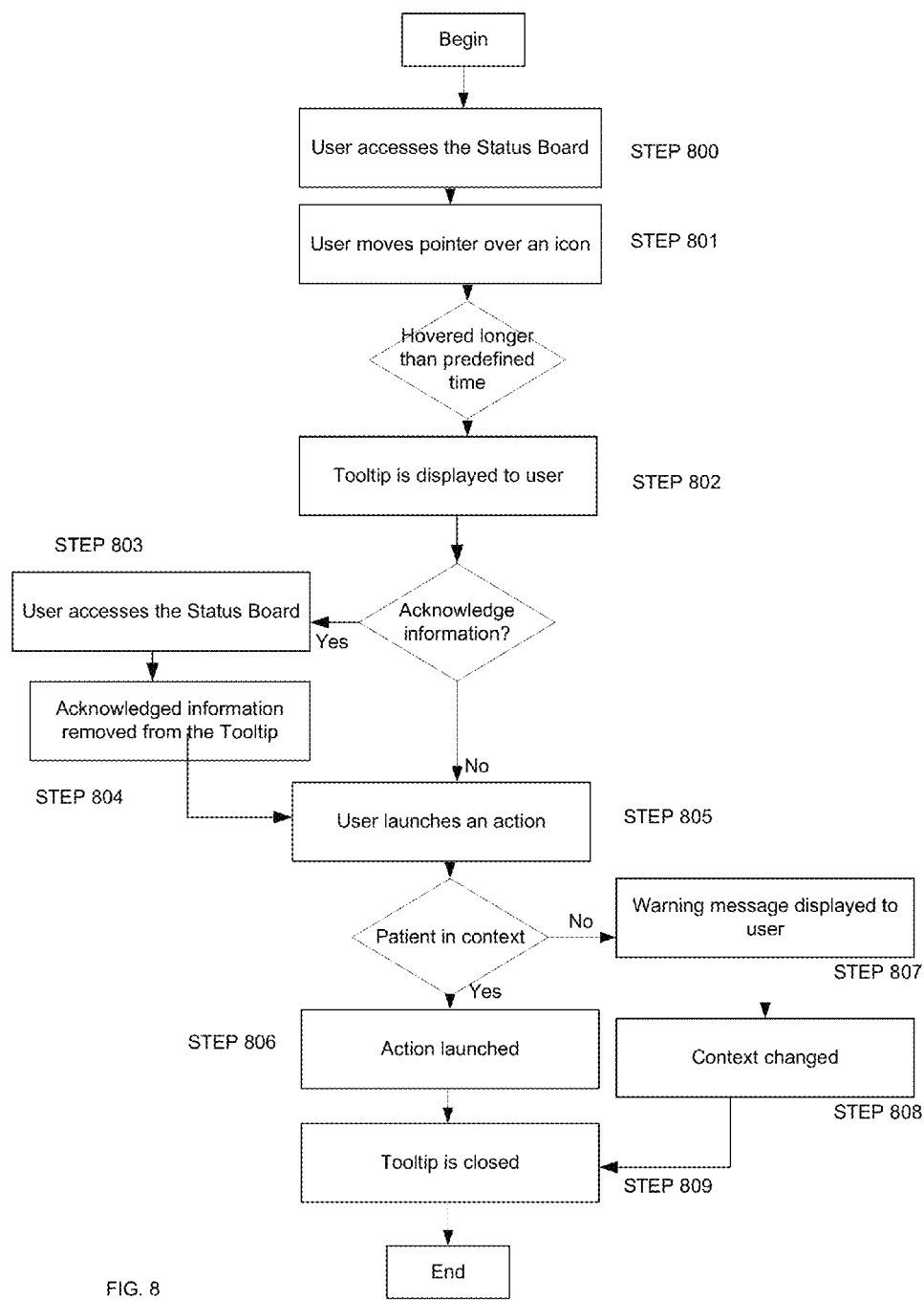
FIG. 8 is an example flow diagram of an implementation of the disclosed Tooltip.

An example flow diagram of an implementation of the disclosed Tooltip is illustrated in FIG. 8. A user, e.g., a clinician, nurse, etc., accesses a Status Board including a plurality of patient names and information. Associated with each patient may be one or more status board icons. STEP 800. The user then moves a pointer over a certain icon associated with a certain patient. STEP 801. If the user keeps the pointer hovered over the icon longer than a predefined period of time, a Tooltip window is displayed relative to the icon. STEP 802. The user may then review the patient related information displayed in the Tooltip relevant to the selected icon.

If the user is required to acknowledge certain information in the Tooltip, the user may acknowledge the information individually or all at once. STEP 803. The acknowledged information is then removed from the Tooltip. STEP 804.

The user may select to launch an action through the Tooltip, for example, Go to Results or Go to Order Entry, STEP 805. If the Tooltip is displayed for a patient in context, the Tooltip is closed, STEP 809 and the action is launched. Step 806. If the patient is not in context, a message is displayed to the user indicating that the context of the Status Board is going to be changed. STEP 807. Once this message is addressed, the context is changed Step 808, the action is launched Step 806 and the Tooltip is closed. STEP 809.

The disclosed Tooltip provides software users access to key information in one consolidated, easy-to-access screen and provides navigation and buttons to quickly act on that information during the course of a user's regular workflow.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof

What is claimed is:

1. A method for accessing information in a healthcare software application using a computing device, the computing device comprising one or more processors, the one or more processors for executing a plurality of computer readable instructions, the computer readable instructions for implementing the method for accessing information, the method comprising the steps of:
    (a) displaying, to a user, an interface comprising a status board listing a plurality of patients;
    (b) determining that the user has selected, within the status board, a first patient of the plurality of patients, and highlighting a portion of the status board associated with the first patient;
    (c) determining that the user's pointer is hovering over an icon associated with a particular patient, the icon associated with icon specific information;
    (d) displaying a tooltip including a header, a display window, and an action button, the action button for launching an action in the application, and displaying the icon specific information for the particular patient in the display window, wherein
        (i) if the particular patient is not the first patient, the header is colored a first color as a visual indication that the displayed tooltip is displaying information for a patient other than the selected patient,
        (ii) if the particular patient is the first patient, the header is not colored the first color;
    (e) detecting that the user has selected the action button; and
    (f) launching the action.

2. The method of claim 1 further comprising deleting the tooltip when the action is launched.

3. The method of claim 2, wherein the tooltip further includes
    a tree section including a section of information for review by the user; and
    a hyperlink for scrolling the section to the top of the display window.

4. A method for accessing information in a healthcare software application using a computing device, the computing device comprising one or more processors, the one or more processors for executing a plurality of computer readable instructions, the computer readable instructions for implementing the method for accessing information, the method comprising the steps of:
    (a) displaying, to a user, an interface comprising a status board listing a plurality of patients;
    (b) determining that the user has selected, within the status board, a first patient of the plurality of patients, and highlighting a portion of the status board associated with the first patient;
    (c) determining that the user's pointer is hovering over an icon associated with a particular patient, the icon associated with icon specific information;
    (d) displaying a tooltip including a header, a display window, and an action button, the action button for launching an action in the application, and displaying the icon specific information for the particular patient in the display window, wherein
        (i) if the particular patient is not the first patient, the header includes a caution symbol indicating that the displayed tooltip is displaying information for a patient other than the selected patient,
        (ii) if the particular patient is not the first patient, the header does not include the caution symbol;
    (e) detecting that the user has selected the action button; and
    (f) launching the action.

5. The method of claim 1, wherein the first color is red.

6. The method of claim 1, wherein the action button is configured to allow a user to "Review All".

7. The method of claim 1, wherein the action button is configured to allow a user to access order entry functionality.

8. The method of claim 1, wherein the action button is configured to allow a user to access results functionality.

9. The method of claim 1, wherein the action button is configured to allow a user to access annotation functionality.

10. The method of claim 4, wherein the action button is configured to allow a user to "Review All".

11. The method of claim 4, wherein the action button is configured to allow a user to access order entry functionality.

12. The method of claim 4, wherein the action button is configured to allow a user to access results functionality.

13. The method of claim 4, wherein the action button is configured to allow a user to access annotation functionality.

14. The method of claim 4 further comprising deleting the tooltip when the action is launched.

15. The method of claim 4, wherein the tooltip further includes
- a tree section including a section of information for review by the user; and
- a hyperlink for scrolling the section to the top of the display window.

* * * * *